US006217885B1

(12) United States Patent
Röder et al.

(10) Patent No.: US 6,217,885 B1
(45) Date of Patent: Apr. 17, 2001

(54) ANTIPRURIGINOUS COSMETIC AND/OR PHARMACEUTICAL COMPOSITIONS CONSISTING OF ONE OR SEVERAL LIGHT LOCAL ANAESTHETICS AND ONE OR SEVERAL ASTRINGENT SUBSTANCES

(75) Inventors: Klaus Röder, Leverkusen; Sabine Koch, Gladbach, both of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/029,114

(22) PCT Filed: Aug. 19, 1996

(86) PCT No.: PCT/EP96/03641

§ 371 Date: Feb. 18, 1998

§ 102(e) Date: Feb. 18, 1998

(87) PCT Pub. No.: WO97/07821

PCT Pub. Date: Mar. 6, 1997

(30) Foreign Application Priority Data

Aug. 30, 1995 (DE) ............................... 195 31 893

(51) Int. Cl.$^7$ ................. A61K 6/00; A61K 7/00
(52) U.S. Cl. ............ 424/401; 514/827; 514/828; 514/829; 514/830; 514/848; 514/886; 514/887; 514/969
(58) Field of Search ............ 424/401; 514/969, 514/848, 827, 828, 829, 830, 886, 887

(56) References Cited

U.S. PATENT DOCUMENTS 4,963,591 * 10/1990 Fourman et al. ............... 514/944
5,676,955 * 10/1997 Ansmann et al. ............... 424/401
5,804,203 * 9/1998 Hahn et al. ...................... 424/401

OTHER PUBLICATIONS

Fiedler, Lexikon der Hilfsstoffe für Pharmazie und Kosmetik und angrenzende Gebiete, Verlag: Editio Canto Aulendorf, 3. Auflage, Band 1, S. 540.

Fiedler, Lexikon der Hilfsstoffe für Pharmazie und Kosmetik und angrenzende Gebiete, Verlag: Editio Cantor Aulendorf, 3. Auflage, Band 1, S. 309.

Aktuel. Dermatol., 1990, 16/8 (221–225), Germany, Federal Republic of, XP000614542, Bergner T. et al., "Prurigo simplex subacuta" p. 223.

Prof. Care Mother Child, May 1994, 4 (4) P109–10, England, XP000614706 Sinclair A: "Remedies for common family ailments: 4. Insect bites and stings." p. 109.

Helwig H.; Hans–Hartwig O.: "Helwig Arzneimittel" 1988, Stuttgart, WVG.; DE XP002023751 pp. 13–37.

Harvey, Topical Drugs, Remington's Pharmaceutical Sciences, 15;716–179, 1975.*

* cited by examiner

Primary Examiner—Thurman K. Page
Assistant Examiner—Todd D. Ware
(74) Attorney, Agent, or Firm—Norris McLaughlin & Marcus

(57) ABSTRACT

The present invention relates to antipruritic cosmetic and/or pharmaceutical compositions for use on human or animal skin, comprising one or more mild local anesthetics, one or more astringents and/or, if appropriate, a substance having an antiinflammatory action.

7 Claims, No Drawings

ANTIPRURIGINOUS COSMETIC AND/OR PHARMACEUTICAL COMPOSITIONS CONSISTING OF ONE OR SEVERAL LIGHT LOCAL ANAESTHETICS AND ONE OR SEVERAL ASTRINGENT SUBSTANCES

The present invention relates to antipruritic cosmetic and/or pharmaceutical compositions for use on human or animal skin.

Insect stings and the associated itching are not only unpleasant, but can also lead to inflammations due to scratching on the itching areas of the skin. The scars often heal with difficulty and are visible for a long time or permanently. Alleviation of the itching is therefore particularly important in order to avoid complications.

It is known from the literature that ethoxylated compounds, such as, for example, laureth-9 (Fiedler, Lexikon der Hilfsstoffe für Pharmazie und Kosmetik und angrenzende Gebiete [Dictionary of auxiliaries for pharmaceuticals and cosmetics and related fields], publisher: Editio Cantor Aulendorf, 3rd edition, volume 1, page 540) or polyoxyethylene (20)-sorbitan monolaurate (manufacturer's data) or substances from other classes of substance, for example citric acid esters (Fiedler, Lexikon der Hilfsstoffe fir Pharmazie und Kosmetik und angrenzende Gebiete [Dictionary of auxiliaries for pharmaceuticals and cosmetics and related fields], publisher: Editio Cantor Aulendorf, 3rd edition, volume 1, page 309), have a certain local anesthetic action. This has also been confirmed in experiments on reducing itching after insect stings (see tables).

Nevertheless, previous antipruritic cosmetic and/or pharmaceutical compositions were not satisfactory because their actions subside rapidly.

The object of the present invention was to provide antipruritic cosmetic and/or pharmaceutical compositions for use on human or animal skin which alleviate swelling of the skin, allow swollen skin to detumesce, prevent reddening, and finally alleviate the itching over a relatively long period of time.

It should furthermore be ensured that the antipruritic cosmetic and/or pharmaceutical compositions according to the invention 1. do not impair the biological processes of the skin,
2. the active compounds do not have a pronounced intrinsic smell,
3. the active compounds are harmless in the event of an overdose or if used otherwise not as intended,
4. the active compounds do not become concentrated in or on the skin after repeated use,
5. the active principles can be incorporated easily into customary cosmetic or dermatological formulations, for example solutions, gels, balms, creams, foams or sticks,
6. the active compounds do not irritate the skin,
7. the active compounds do not interact with clothing materials.

It has now been found, and therein lies the achievement of all the abovementioned objects, that the use of an active complex comprising one or more mild local anesthetics, one or more astringents, for example the tanning agent tannin, and/or, if appropriate, a substance having an antiinflammatory action persists for much longer than was to be expected from the sum of the activity of the individual components. While the average antipruritic action of laureth-9 persists for about 30 minutes, tannin by itself indeed caused the skin to detumesce and alleviated reddening, but acted against the itching only indirectly (for less than 10 minutes after the application), and glycyrrhizinate and bisabolol also acted against the itching for only about 5 minutes, the action of the combination of the individual components persisted for up to 3 hours (average per 5 subjects: 130 to 140 minutes).

The compositions according to the invention are therefore outstandingly suitable for alleviating itching, for example after insect stings, contact with stinging nettles and jellyfish, and with allergic skin reactions. They counteract reddening of the skin and additionally have a detumescent action. It has furthermore been found that the cosmetic and/or pharmaceutical dermatological agents according to the invention display a potent action against development of erythema after excessive UV irradiation.

Preferred compositions according to the invention comprise 1. one or more local anesthetics of the series consisting of laureth-9, polyoxyethylene (20)-sorbitan monolaurate, triethyl citrate, acetyl-triethyl citrate, tributyl citrate or acetyl-tributyl citrate,
2. one or more astringents from the series consisting of tannin, walnut leaf extract, aluminum lactate or sodium tartrate and/or, if appropriate,
3. one or more substances having an antiinflammatory action from the series consisting of Dragosantol®, bisabolol, panthenol, pantothenyl alcohol, glycyrrhetin derivatives, glycyrrizin derivatives or liquorice extract.

Particularly preferred compositions according to the invention comprise 1. one or more local anesthetics of the series consisting of laureth-9, polyoxyethylene (20)-sorbitan monolaurate, triethyl citrate, acetyl-triethyl citrate, tributyl citrate or acetyl-tributyl citrate,
2. one or more astringents from the series consisting of tannin, walnut leaf extract, aluminum lactate or sodium tartrate and/or, if appropriate,
3. one or more substances having an antiinflammatory action from the series consisting of Dragosantol®, bisabolol, panthenol, dexpanthenol, pantothenyl alcohol, dipotassium glycyrrhizinate, glycyrrhizinic acid or salts thereof, glycyrrhetic acid or salts thereof, stearyl glycyrrhetinate or liquorice extract.

The active complex comprising laureth-9, tannin, dipotassium glycyrrhizinate and/ or bisabolol is particularly preferred.

All the components are known from the literature. Some of the contents are briefly described specifically:

Laureth-9 is a polyethylene glycol (9)-monododecyl ether (polydocanol), an adduct of 9 mol of ethylene oxide onto dodecyl alcohol; it corresponds to the formula

$$C_{13}H_{25}-(O-CH_2-CH_2)_n-OH$$

(n has an average value of 9), and the average molecular weight is about 600.

Dragosantol® is a trade name for a synthetically prepared, colorless to pale yellowish-colored, faintly smelling liquid, (−)-α-bisabolol [(−)-6-methyl-2-(4-methyl-3-cyclohexenyl)-5-hepten-2-ol]

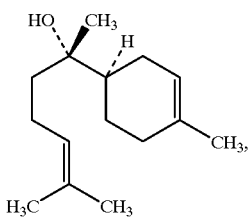

glycyrrhetic acid (3β-hydroxy-11-oxoolean-12-en-30-oic acid, common name: enoxolone, biosone).

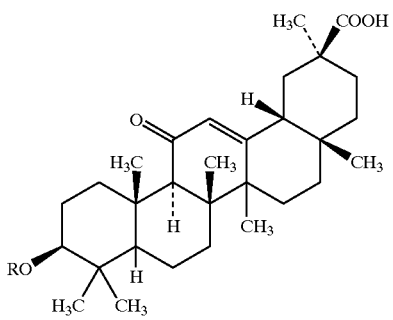

R=H: glycyrrhetic acid

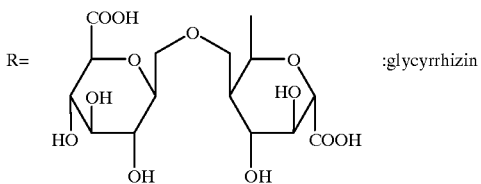

:glycyrrhizin

The antipruritic cosmetic and/or pharmacological compositions according to the invention comprise the additives and solutions customary for topical use, preferably as liquid, semi-solid or solid formulations.

Drops, tinctures or sprays, each of which comprise the active compound mixtures described above in the form of a solution, suspension, emulsion or dispersion, are possible for the liquid formulation.

Possible semi-solid formulations are, for example, gels, ointments, creams or foams, while solid formulations include, for example, powders, dusting powders, granules, pellets or microcapsules. If the active compound mixtures described above are available as a pharmaceutical and/or cosmetic composition in the form of a liquid presentation form, it is advisable to use for these, as far as possible, those diluents which do not irritate the skin when used topically. This applies in particular, for example, to water, monohydric alcohols, preferably ethanol, isopropanol or n-propanol, polyhydric alcohols, in particular glycerol and/or propanediol, polyglycols, in particular polyethylene glycols and/or Miglyol, glycerol formal, dimethylisosorbitol, naturally occurring and synthetic oils and/or esters.

In addition to the abovementioned diluents, base masses, such as, for example, bentonite, Veegum, guar flour and/or cellulose derivatives, in particular methylcellulose and/or carboxymethylcellulose, are also suitable for the preparation of semi-solid presentation forms, such as, for example, gels, ointments, creams and foams. Instead of the abovementioned base masses or in addition to the abovementioned base masses, possible base masses are also polymers of vinyl alcohols, vinylpyrrolidones, alginates, pectins, polyacrylates, solid and/or liquid polyethylene glycols, paraffins, fatty alcohols, vaseline, waxes, fatty acids and/or fatty acid esters.

For the preparation of solid formulations which are also suitable for topical use, such as, for example, the abovementioned powders, dusting powders, granules, pellets or microcapsules, there is the possibility of using here, for example, colloidal salicylic acid, talc, lactose, starch powder, sugars, cellulose derivatives, gelatin, metal oxides and/or metal salts as binders.

The compositions according to the invention can furthermore optionally also comprise further constituents, such as, for example, preservatives, stabilizers, surfactants, emulsifiers, penetration promoters, spreading agents and/or propellants.

The compositions according to the invention can be employed against the concomitant symptoms of allergic skin reactions and of neurodermatitis, and for alleviating the symptoms following contact with, for example, stinging nettles or jellyfish.

However, in the case of insect stings in particular, thus, for example, bee stings, wasp stings, hornet stings, mosquito bites, mite bites, tick bites, sand flea bites, biting fly bites and horse fly bites, it has been found that a significant decrease in the reddening, swellings and/or wealing caused by the abovementioned stings and bites already occurs after a very short time after application of the compositions according to the invention, while at the same time the pain stimulus and itching caused by the insect sting or insect bite is reduced significantly.

No undesirable irritation or reddening of the skin was to be found after topical use of the compositions according to the invention even on very sensitive patients.

The cosmetic and/or pharmaceutical compositions according to the invention can be in various forms, such as are usually employed, for example, for this type of formulation. Thus, they can be, for example, an aqueous, alcoholic or aqueous-alcoholic solution, an emulsion of the water-in-oil (W/O) type or of the oil-in-water (O/W) type, or a multiple emulsion, for example of the water-in-oil-in-water (W/O/W) type, a gel, a hydrodispersion, a solid stick or also an aerosol.

The compositions according to the invention can comprise cosmetic auxiliaries such as are usually used in such formulations, for example preservatives, bactericides, perfumes, agents for preventing foaming, dyestuffs, pigments which have a coloring action, thickeners, surface-active substances, emulsifiers, softening substances, moistening and/or humectant substances, fats, oils, waxes or other customary constituents of a cosmetic formulation such as alcohols, polyols, polymers, foam stabilizers, electrolytes, organic solvents or silicone derivatives.

If the cosmetic and/or pharmaceutical compositions according to the invention are a solution or lotion, solvents which can be used are:

water or aqueous solutions;

oils, such as triglycerides of capric or of caprylic acid, but preferably vegetable oils, such as, for example, castor oil, rape oil and the like;

fats, waxes and other naturally occurring and synthetic fatty substances, preferably esters of fatty acids with alcohols of low C number, for example with isopropanol, propylene glycol or glycerol, or esters of fatty alcohols with alkanoic acids of low C number or with fatty acids;

alcohols, diols or polyols of low C number, and ethers thereof, preferably ethanol, isopropanol, propylene glycol, glycerol, ethylene glycol, ethylene glycol monoethyl or monobutyl ether, propylene glycol monomethyl, monoethyl or monobutyl ether, diethylene glycol monomethyl or monoethyl ether and analogous products.

Mixtures of the abovementioned solvents are used in particular. In the case of alcoholic solvents, water can be a further constituent.

The cosmetic and/or pharmaceutical compositions according to the invention can also be in the form of gels or hydrodispersions which, in addition to the active compound combinations according to the invention, also comprise organic thickeners, for example gum arabic, xanthan gum, sodium alginate or cellulose derivatives, preferably methylcellulose, hydroxymethylcellulose, hydroxyethylcellose, hydroxypropylcellulose or hydroxypropylmethylcellulose, or inorganic thickeners, for example aluminum silicates, such as, for example, bentonites, or a mixture of polyethylene glycol and polyethylene glycol stearate or distearate. The gel comprises the thickener, for example, in an amount of between 0.1 and 30% by weight, preferably between 0.5 and 15% by weight.

Gels according to the invention usually comprise alcohols of low C number, for example ethanol, isopropanol, 1,2-propanediol, glycerol and water, or an abovementioned oil in the presence of a thickener, which, in the case of oily-alcoholic gels, is preferably silicon dioxide or an aluminum silicate and, in the case of aqueous-alcoholic or alcoholic gels, is preferably a polyacrylate.

Hydrodispersions are dispersions of a liquid, semi-solid or solid internal (discontinuous) lipid phase in an external aqueous (continuous) phase.

In contrast to O/W emulsions, which are distinguished by a similar phase arrangement, however, hydrodispersions are essentially free from emulsifiers. Hydrodispersions, as are also emulsions otherwise, are metastable systems and tend to convert into a state of two discrete phases which are continuous in themselves. In emulsions, the choice of a suitable emulsifier prevents phase separation.

In hydrodispersions of a liquid lipid phase in an external aqueous phase, the stability of such a system can be guaranteed, for example, by building up in the aqueous phase a gel matrix in which the lipid droplets are suspended in stable form.

Solid sticks according to the invention can comprise, for example, naturally occurring or synthetic waxes, fatty alcohols or fatty acid esters.

Suitable propellants for cosmetic or dermatological formulations according to the invention which can be sprayed from aerosol containers are the customary known readily volatile liquefied propellants, for example hydrocarbons (propane, butane and isobutane), which can be employed by themselves or as a mixture with one another. Compressed air can also advantageously be used.

The expert of course knows that there are non-toxic propellant gases which would in principle be suitable for the present invention but which should nevertheless be omitted because of an unacceptable action on the environment or other concomitant circumstances, in particular fluorohydrocarbons and fluorochlorohydro-carbons (CFCs).

The cosmetic and/or pharmaceutical compositions according to the invention preferably comprise, in addition to the base substances and auxiliaries customary for skin care compositions, 0.1 to 30% of local anesthetics, for example laureth-9

0.1 to 30% of astringents, for example tannin, and, if appropriate, 0.05 to 10% of substances having an antiinflammatory action, such as, for example, bisabolol and/or dipotassium glycyrrhizinate.

The cosmetic and/or pharmaceutical compositions according to the invention particularly preferably comprise, in addition to the base substances and auxiliaries customary for skin care compositions, 0.1 to 20% of local anesthetics, 0.1 to 20% of astringents, 0.05 to 10% of one or more substances having an antiinflammatory action.

The compositions according to the invention furthermore comprise base substances and auxiliaries.

The base substances and auxiliaries include the customary solvents in cosmetics already mentioned above, such as water up to the extent of 70%, monoalcohols, lower polyalcohols having 1 to 6 carbon atoms or mixtures thereof, and furthermore fatty substances, such as mineral, animal, or vegetable oils, such as paraffin oil, or waxes, such as microwax, fatty acids, fatty alcohols, fatty acid esters, such as cetylstearyl isononanoate and isopropyl palmitate, fatty alcohol ethers, oxyethylated fatty alcohols, lanolin and derivatives, as well as silicone oils in amounts of 0.5 to 50%, preferably 0.5 to 30%, particularly preferably in amounts of 5 to 30%.

If appropriate, the compositions according to the invention comprise emulsifiers in amounts of 0.1 to 20%, preferably in amounts of 0.2 to 10%, the emulsifiers being those such as are usually used in cosmetics, in particular nonionic, anionic, cationic or amphoteric compounds, for example sterols, polyol-fatty acid esters and fatty alcohol ethers, alkali metal and triethanolamine salts of fatty acids, sodium cetylstearyl sulfate, tetraacylammonium halides and phospholipids. Examples of these are glycerol sorbitan fatty acid esters, polyoxyethylene fatty acid esters and alkyltetraglycol ether-o-phosphoric acid esters.

0.02 to 5%, preferably 0.1 to 2%, of thickeners and gelling agents can furthermore be employed to the compositions according to the invention. These include polyacrylic acid derivatives, cellulose derivatives, bentonites, xanthan derivatives, alginates, guar flour and carob bean flour. Examples are polyacrylamide and zinc stearate.

As already mentioned above, the preparation according to the invention can comprise other substances customary in cosmetic compositions. These include humectants (0.5 to 15%), dyestuffs, buffer substances, preservatives and perfume oils in amounts of 0.01 to 5.0%.

Examples of humectants which may be mentioned are: lower polyalcohols, such as glycerol, propylene glycol, butylene glycol and sorbitol, and furthermore 2-pyrrolidone-5-carboxylic acid and its sodium salt, lactic acid and its salts, urea, proteins and protein derivatives, such as collagen, and furthermore hyaluronic acid and the like.

Examples which may be mentioned of dyestuffs to be added to the cosmetic and/or pharmaceutical preparations according to the invention are:

Color C.I. 16255, color C.I. 61570, color C.I. 42051, color C.I. 15985 and color C.I. 77492.

Possible preservatives are, preferably:

2,4-hexadienoic acid (sorbic acid and its salts), 4-hydroxybenzoic acid, its salts and esters, 3-acetyl-6-methyl-2,4(3H)-pyrandione (dehydracetic acid) and its salts, 1,1-methylene-bis-(3-(1-hydroxymethyl-2,4-dioximidazolin-5-yl)-urea), imidazolidinylurea, 2-phenoxy-ethanol, benzyl alcohol.

The compositions according to the invention are preferably in the form of a solution or emulsion (cream or milk), which can be an oil-in-water or water-in-oil emulsion.

The compositions according to the invention are prepared by customary processes. In these processes, the actual active substances are initially introduced into the preparation vessel and are mixed with the customary base substances and auxiliaries, if appropriate with predispersion, stirring and/or homogenization, if appropriate in an evacuated apparatus.

All the percentage data in the present text are based on percentages by weight, unless stated otherwise.

The invention is illustrated in more detail below with the aid of the examples, without these being intended to have a limiting character.

RECIPE EXAMPLES

EXAMPLE 1

Antipruritic preparation comprising 0.5 to 20% of laureth-9

0.1 to 15% of tannin and, if appropriate, 0.05 to 3% of dipotassium glycyrrhizinate and/or 0.05 to 3% of bisabolol.

EXAMPLE 2

Recipe for an antipruritic solution

| | |
|---|---|
| laureth-9 | 3.50% |
| tannic acid | 5.00% |
| bisabolol | 0.40% |
| ethanol | 30.00% |
| 1,3-butylene glycol | 5.00% |
| perfume | q.s. |
| water | to 100.00% |

EXAMPLE 3

Recipe for an antipruritic gel

| | |
|---|---|
| laureth-9 | 6.00% |
| tannic acid | 1.50% |
| dipotassium glycyrrhizinate | 1.00% |
| carbopol 2984 ® | 0.70% |
| sodium hydroxide solution, 45% strength | 0.05% |
| ethanol | 30.00% |
| glycerol | 10.00% |
| perfume/preservative | q.s. |
| water | to 100.00% |

Activity test

Mosquito bites (Aedes aegypti) were provoked on both dorsal underarms of volunteer persons under controlled conditions. In the blind test, in each case one arm was treated with placebo and one arm was treated with active compound solution. The test persons evaluate the test products in respect of the duration of alleviation of itching.

Recipes

A: Placebo (base recipe)

| | |
|---|---|
| water | 57.00% |
| glycerol | 3.00% |
| ethanol | 40.00% |

B: Base recipe+laureth-9

| | |
|---|---|
| water | 57.00% |
| glycerol | 3.00% |
| ethanol | 40.00% |
| laureth-9 | 5.00% |

C: Base recipe+tannin

| | |
|---|---|
| water | 55.00% |
| glycerol | 3.00% |
| ethanol | 40.00% |
| tannic acid | 2.0% |

D: Base recipe+dipotassium glycyrrhizinate

| | |
|---|---|
| water | 56.90% |
| glycerol | 3.00% |
| ethanol | 40.00% |
| dipotassium glycyrrhizinate | 0.10% |

E: Base recipe+bisabolol

| | |
|---|---|
| water | 56.90% |
| glycerol | 3.00% |
| ethanol | 40.00% |
| bisabolol | 0.10% |

F: Combination 1 of these active compounds

| | |
|---|---|
| water | 49.80% |
| glycerol | 3.00% |
| ethanol | 40.00% |
| laureth-9 | 5.00% |
| tannic acid | 2.00% |
| dipotassium glycyrrhizinate | 0.10% |

G: Combination 2 of these active compounds

| | |
|---|---|
| water | 49.80% |
| glycerol | 3.00% |
| ethanol | 40.00% |
| laureth-9 | 5.00% |
| tannic acid | 2.00% |
| bisabolol | 0.10% |

Results

Duration of the alleviation of itching

| Subject | A: Placebo in minutes | B: Laureth 9 in minutes |
|---|---|---|
| 1 | 0 | 25 |
| 2 | 10 | 30 |
| 3 | 0 | 60 |
| 4 | 5 | 15 |
| 5 | 10 | 20 |
| Average | 5 | 30 |

| Subject | A: Placebo in minutes | C: Tannin in minutes |
|---|---|---|
| 1 | 5 | 0 |
| 2 | 0 | 15 |
| 3 | 0 | 5 |
| 4 | 10 | 20 |
| 5 | 0 | 5 |
| Average | 3 | 9 |

| Subject | A: Placebo in minutes | D: Dipotassium glycyrrhizinate in minutes |
|---|---|---|
| 1 | 0 | 10 |
| 2 | 10 | 5 |
| 3 | 0 | 0 |
| 4 | 10 | 15 |
| 5 | 5 | 10 |
| Average | 5 | 8 |

| Subject | A: Placebo in minutes | E: Bisabolol in minutes |
|---|---|---|
| 1 | 10 | 10 |
| 2 | 0 | 5 |
| 3 | 15 | 5 |
| 4 | 15 | 5 |
| 5 | 0 | 5 |
| Average | 8 | 6 |

| Subject | A: Placebo in minutes | F: Combination 1 in minutes |
|---|---|---|
| 1 | 0 | 90 |
| 2 | 10 | 120 |
| 3 | 15 | 190 |
| 4 | 0 | 160 |
| 5 | 0 | 90 |
| Average | 5 | 130 |

| Subject | A: Placebo in minutes | G: Combination 2 in minutes |
|---|---|---|
| 1 | 0 | 115 |
| 2 | 10 | 90 |
| 3 | 15 | 210 |
| 4 | 0 | 160 |
| 5 | 0 | 125 |
| Average | 5 | 140 |

What is claimed is:

1. An antipruritic composition comprising:

a) a local anesthetic consisting of polyethylene glycol (9)-monododecyl ether; sorbitan b) one or more astringents selected from the group consisting of tannin, walnut leaf extract, aluminum lactate and sodium tartrate; or c) one or more antiinflammatory substances selected from the group consisting of bisabolol, panthenol, glycyrrhizinic acid, glycyrrhizinic acid salts, glycyrrhetic acid, glycyrrhetic acid salts, stearyl glycyrrhetinate and liquorice extract.

2. An antipruritic composition according to claim 1, which comprises one or more substances selected from the group consisting of polyethylene glycol (9)-monododecyl ether, tannin, dipotassium glycyrrhizinate and bisabolol.

3. An antipruritic composition according to claim 1, which is in the form of a liquid, semi-solid or solid formulation.

4. The antipruritic composition according to claim 1 comprising:

a) 0.1 to 30% of the weight of the composition of polyethylene glycol (9)-monododecyl ether;

b) 0.1 to 30% of the weight of the composition of one or more said astringents; and c) 0.05 to 10% of the weight of the composition of one or more said antiinflammatory substances.

5. An antipruritic composition according to claim 1, which further comprises one or more base substances or auxiliaries selected from the group consisting of emulsifiers, thickeners, gelling agents, humectants, dyestuffs, buffer substances, preservatives, perfume oils, stabilizers, surfactants, spreading agents and propellants.

6. A method of treating pruritus resulting from an insect bite or skin damage caused by light or heat, said method comprising applying to affected skin an effective amount therefor of a composition according to any one of claims 1–5.

7. A process for the preparation of an antipruritic composition according to claim 1, said process comprising introducing a local anesthetic, one or more astringents and one or more antiinflammatory substances into a preparation vessel in any order to produce a mixture of active ingredients, and mixing said mixture of active ingredients with one or more base substances and auxiliaries, optionally with predispersion, stirring and/or homogenization, and optionally in an evacuated apparatus.

* * * * *